United States Patent [19]

Sepponen

[11] Patent Number: 5,218,964
[45] Date of Patent: Jun. 15, 1993

[54] METHOD FOR PROVIDING ACCURATE REFERENCE MARKERS IN MAGNETIC RESONANCE IMAGES

[75] Inventor: Raimo Sepponen, Helsinki, Finland

[73] Assignee: Instrumentarium Corp., Finland

[21] Appl. No.: 738,834

[22] Filed: Aug. 1, 1991

Related U.S. Application Data

[63] Continuation-in-part of Ser. No. 421,951, Oct. 16, 1989, abandoned.

[30] Foreign Application Priority Data

Oct. 21, 1988 [FI] Finland .................................. 884861

[51] Int. Cl.⁵ .......................................... A61B 5/055
[52] U.S. Cl. .............................. 128/653.2; 128/653.4; 324/309
[58] Field of Search .................. 128/653.2, 653.4; 324/309, 307

[56] References Cited

U.S. PATENT DOCUMENTS

| | | | |
|---|---|---|---|
| 4,617,925 | 10/1986 | Laitinen | 128/303 |
| 4,719,425 | 1/1988 | Ettinger | 324/316 |
| 4,984,573 | 1/1991 | Leunbach | 128/653.4 |
| 4,989,608 | 2/1991 | Ratner | 128/653 |
| 4,991,579 | 2/1991 | Allen | 128/653 |

OTHER PUBLICATIONS

J. Potenza, "Measurement and Applications of Dynamic Nuclear Polarization", Advan. Mol. Relaxation Processes, vol. 4, pp. 229-354.

Lepley, A. R. and Closs, G. L., "Chemically Induced Magnetic Polarization", New York, 1973.
Maciel, G. E. et al., "NMR Imaging of Paramagnetic Centers in Solids via Dynamic Nuclear Polarization", J. Magn. Reson., vol. 64, pp. 356-360, 1985.
Lurie, D. J., et al., "Proton-Electron Double Magnetic Imaging of Free Radical Solutions", J. Magn. Reson., vol. 76, pp. 366-370, 1988.
Lurie, D. J., et al., "Proton Electron Double Resonance Imaging: A New Method for Imaging Free Radicals", Proc. S.M.R.M. Fifth Annual Meeting, 1987, New York, p. 24.

*Primary Examiner*—Ruth S. Smith
*Attorney, Agent, or Firm*—Andrus, Sceales, Starke & Sawall

[57] ABSTRACT

A method for providing reference markers in magnetic resonance (MR) images which are highly discernible and accurately defined in the MR image. The method may be carried out with short imaging times. The reference markers have a volume containing NMR active nuclei and an electron spin resonance relaxant. During the MRI examination procedure of an object, electron spin resonance energy is supplied to the reference markers to amplify the NMR signal from the markers by dynamic nuclear polarization. The amplification improves the visibility of the reference marker in the MR image of the object while permitting the size of the marker to be reduced to improve the accuracy by which other features appearing in the image may be located by reference to the markers. The reference markers may be used to locate anatomical features in a portion of a human body undergoing MRI examination.

15 Claims, 3 Drawing Sheets

METHOD FOR PROVIDING ACCURATE REFERENCE MARKERS IN MAGNETIC RESONANCE IMAGES

The present application is a continuation-in-part application of U.S. patent application Ser. No. 07/421,951, filed Oct. 16, 1989 and now abandoned.

The present invention relates to a method for providing reference markers in magnetic resonance (MR) images which are highly discernible and which permit features appearing in the MR image to be located, by reference to the markers, with a high degree of accuracy. The method may be carried out with short imaging times. Typically, the reference markers may be used to locate anatomical features in a portion of the human body undergoing MRI examination. The resulting information is used for diagnostic, therapeutic, surgical or other purposes.

Magnetic resonance imaging (MRI) is a technique which exploits the nuclear magnetic resonance phenomenon (NMR) for the determination of the nuclear density of an object and the NMR characteristics associated with a nucleus or the local distributions of physical and chemical characteristics affecting the same. Said NMR characteristics include e.g.: longitudinal relaxation (characterized by longitudinal relaxation time T1), transverse relaxation (characterized by transverse relaxation time T2), relaxation in the rotating frame of reference (characterized by relaxation time T1rho), chemical shift, and coupling factors between the nuclei. NMR characteristics are affected by the physico-chemical environment of the nuclei: polarizing magnetic field $B_o$, flow rate, diffusion, paramagnetic materials, ferromagnetic materials, viscosity and temperature.

Methods and applications of magnetic resonance and magnetic resonance imaging have been studied in a number of references: Poole C P and Farach H A; Theory of magnetic resonance, John Wiley, New York 1987; Stark D D and Bradley W G, Magnetic resonance imaging, C. V. Mosby Comp., St. Louis 1988; Gadian D G, Nuclear magnetic resonance and its applications to living systems, Oxford Univ. Press, London 1982; Shaw D, Fourier transform NMR spectroscopy, Elsevier, Amsterdam 1984; Battocletti J H, NMR proton imaging, CRC Crit. Rev. Biomed. Eng. vol. 11, pp. 313-356, 1984; Mansfield P and Morris P G, NMR imaging in biomedicine, Adv. in magnetic resonance, Academic Press, New York 1982; Abragam A, the principles of nuclear magnetism, Clarendon press, Oxford 1961; Fukushima E and Roeder S B W, Experimental Pulse NMR, Addison-Wesley, Readin, Mass. 1981; Lasker S E and Milvy P (eds.), Electron spin resonance and nuclear magnetic resonance in biology and medicine and magnetic resonance in biological systems, Annals of New York Academy of Sciences, New York 1973; Sepponen RE, Discrimation and characterization of biological tissues with magnetic resonance imaging: A study on methods for T1, T2, T1rho and chemical shift imaging, Acta Polytechnical Scandinavica EL-56, Helsinki 1986; Fukushima E and Roeder SB, Experimental Pulse NMR, Addison Wesley, London 1981; Anderson WA et al, U.S. Pat. No. 3,475,680; Ernst R R, U.S. Pat. No. 3,501,691; Tomlinson B L et al, U.S. Pat. No. 4,034,191; Ernst R R, U.S. Pat. No. 3,873,909; Ernst R R, U.S. Pat. No. 4,070,611; Bertrand R D et al, U.S. Pat. No. 4,345,207; Young I R, U.S. Pat. No. 4,563,647; Hofer D C et al, U.S. Pat. No. 4,110,681; Savelainen M K, Magnetic resonance imaging at 0.02 T: Design and evaluation of radio frequency coils with wave winding, Acta Polytechnica Scandinavica Ph 158, Helsinki 1988; Sepponen R E, U.S. Pat. No. 4,743,850; Sepponen R E, U.S. Pat. No. 4,654,595; Savelainen M K, U.S. Pat. No. 4,712,068; Sepponen R E, U.S. Pat. No. 4,587,493; Savelainen M K, U.S. Pat. No. 4,644,281; and Kupiainen J, U.S. Pat. No. 4 668 904.

In addition to the above, dynamic nuclear polarization has been studied e.g. in the following references: Lepley A R and Closs G L, Chemically induced magnetic polarization, Wiley, New York 1973, and Potenza J, Measurement and Applications of dynamic nuclear polarization, Adv. Mol. Relaxation Processes vol. 4, Elsevier, Amsterdam 1972, pp. 229-354.

DNP is a magnetic double resonance method which thus requires two separate spin populations. Such spin populations include e.g. the spins of electrons and of protons. In a double resonance method, the distribution of one spin population on various energy levels is changed and the other spin population is observed. As certain conditions are fulfilled, the resonance signal of the observed spin population increases (Overhauser phenomenon). The amplified signal may have an amplitude which is several times higher than the unamplified signal. The amplification factor may be positive or negative. The amplified signal is in its characteristics highly sensitive to the physico-chemical properties and reactions of a spin environment, so its application to the examination of the chemical properties of a material is obvious.

The reference Maciel G E, Davis M P, NMR imaging of paramagnetic centers in solids via dynamic nuclear polarization, J. Magn. Reson., vol. 64, pp. 356-360, 1985 discloses a method suitable for mapping paramagnetic components by combining the DNP and MRI methods. The reference Ettinger K V, U.S. Pat. No. 4,719,425 discloses as applications the mappings of the contents of paramagnetic components and the activity of cerebral nerve cells. The references Lurie D J, Bussel D M, Bell L H, Mallard J R, Proton Electron Double Resonance Imaging: A new method for imaging free radicals, Proc. S.M.R.M. Fifth Annual Meeting, 1987, New York, p. 24 and Lurie D J, Bussel D M, Bell L H, Mallard J R, Proton-Electron Double Magnetic Imaging of free radical solutions, J. Magn. Reson., vol. 76, 1988, pp. 366-370 disclose the mappings of free radical groups, nitroxide radicals and degree of oxidation as possible applications.

According to the prior art, the electron spin system is saturated by radiating the object at a frequency which corresponds to the electron spin resonance or ESR frequency in field $B_o$ and by detecting the NMR signal at an NMR frequency which corresponds to field strength $B_o$. For example, the corresponding frequencies for $B_o$ strength of 0.04 T are ESR frequency of 1.12 GHz and NMR frequency of 1.7 MHz.

Already known are methods suitable for so-called high-speed magnetic imaging, which are introduced e.g. in the following references Rzedzian R R et al, Lancet, December 3, p. 1281, 1983; Haase A et al, J. Magn. Reson. vol. 67, p. 258, 986; Pykett IL et al, Magn. Reson. in Med., vol. 5, p. 563, 1987.

It has been known to employ frames that are fixed relative to the object, e.g. the anatomy of a patient, for creating a positional system of coordinates. An example of such a frame is the stereotactic frames developed for use in connection with cerebral surgery operations by means of x-ray, tomographic x-ray, computerized axial tomography, and magnetic resonance images. Such a frame is attached to the skull of a patient, said frame having reference points visible in such images. The reference points can be used for localizing volumes, such as a tumor, vessel, or other anatomical feature within the skull, or other object, by utilizing the above images. The resulting information may be used for medical procedures.

For the foregoing purpose, parts of such frames are provided with a material detected in imaging for providing the reference points. Prior art products of this type include Leksell Stereotactic Instrument, manufactured by Elekta Instrument AB, Stockholm, Sweden and Orfit Raycast thermoplastic, used e.g. in actinotherapy for positioning a patient, the latter being manufactured by Luxilon Industries & Co., Antwerpen, Belgium. The application of stereotactic methods has been described in the references: Leksell et al, Stereotaxis and nuclear magnetic resonance, J. Neurology, Neurosurgery and Psychiatry, vol. 48, pp. 14-18, 1985; Lehmann and Hill, Computed-tomography-directed stereotaxis for movement disorder with postoperative magnetic resonance imaging confirmation, Appl. Neurophysiol., vol. 51: pp. 21-28, 1988; Kelly et al, Evolution of contemporary instrumentation for computer assisted stereotactic surgery, Surg. Neurol., vol. 27, Fasc 3, 269-274, 1988.

A problem in the prior art is the weak signal-to-noise ratio existing in MRI with respect to the reference points or markers. To provide an adequate signal for imaging purposes, the portions of the frame visible with MRI must contain a correspondingly sufficient volume of a material detectable in MRI, typically the volume of several image voxels. However, such volumes reduce the accuracy of the markers in the MR image with a resulting loss of accuracy in localizing the feature within the object being examined. Ideally, the volume of the marker should be less than the volume of one image voxel. Also, in the prior art, the imaging time must be long. This results in further inaccuracies due to patient movement and the like.

The object of the present invention is, therefore, to provide a method by which highly discernible reference markers may be made to appear in MR images and from which accurate locational data may be obtained.

More specifically, it is an object of the present invention to provide a method by which the markers may be small, for example, less than one image voxel, while at the same time, nuclear magnetic resonance signal levels produced by the markers increased. The reference markers thus appear in the MR image of an object with high visibility and small size, thereby to permit accurate location of features within the object by reference to the markers.

To the foregoing ends, the method of the present invention employs reference markers, the NMR signals of which may be amplified by dynamic nuclear polarization (DNP). The markers may be applied to, or inserted in the object being examined to produce reference areas in the two dimensional MR image. The markers comprise a volume which contains NMR active nuclei and an activating agent or relaxant, which, when stimulated, amplifies the resonance signal obtained from the NMR active nuclei. The amplification increases NMR output signal levels, while at the same time, permits the size of the markers to be reduced. Highly accurate definition of the markers in the MR image can thus be obtained.

The invention will now be described in more detail with reference made to the accompanying drawings, in which:

FIG. 1 shows a patient, or other object, P to be examined, as well as an immobilizing frame F attached to the patient. Patient P is held in a given position with respect to frame F by supports S.

The portion of the patient to be examined, such as the skull, is placed in a polarizing magnetic field $B_o$ generated by an electromagnet M. A current source MC supplies power to the electromagnet M; the action of said field creating in the object a nuclear magnetization and a magnetization produced by electron spins. It will be appreciated that the polarizing magnetic field $B_o$ may be generated by a resistive, permanent, or superconductive magnet. Use of even the earth's magnetic field is sometimes possible.

The object P and frame F are further surrounded by gradient coils GC for generating gradient fields, the strength of which is controlled by an NMR transmitter/receiver and control NMRC through gradient current sources G. In so-called rotating frame zeugmatography, some of the gradients are generated at an NMR excitation frequency.

NMR transmitter/receiver and control NMRC also controls the application of radio frequency to object P via antenna means A necessary to obtain NMR signals from object P. NMR transmitter/receiver and control NMRC further controls a radio frequency transmitter ESRE producing the electron spin resonance energy, i.e. saturation energy which saturates the relaxant electron spin system in the material contained in the hereinafter described reference markers of frame F. The NMR transmitter/receiver and control NMRC is provided with necessary radio frequency components for the procedures required for creating and receiving the NMR signals via antenna means A as well as for storing and processing the signals. The final resulting image is shown on a display D.

Figure 1:
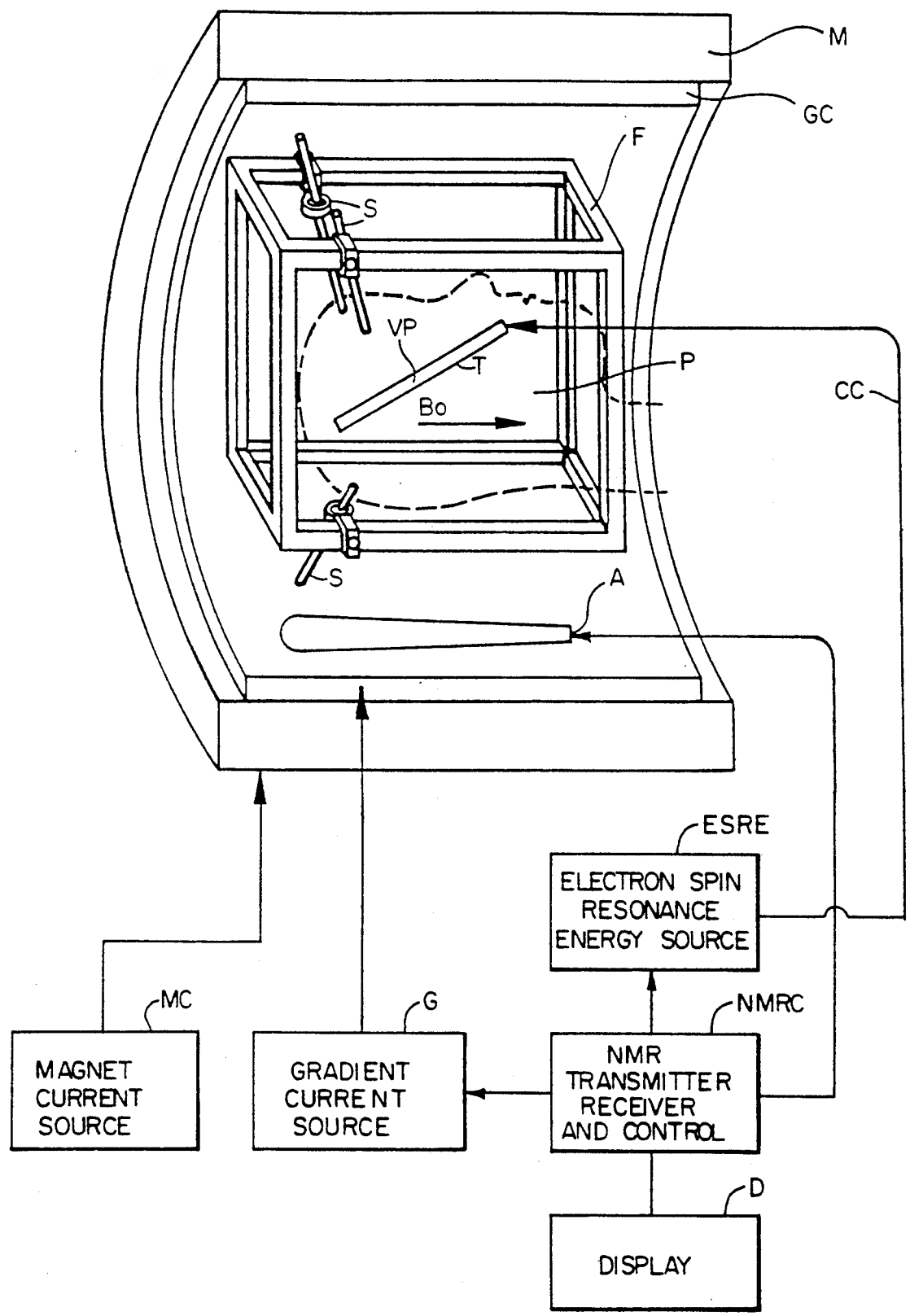
FIG. 1 shows a frame and other elements of a magnetic resonance imaging apparatus suitable for use in the method of the present invention.
Figure 2A:
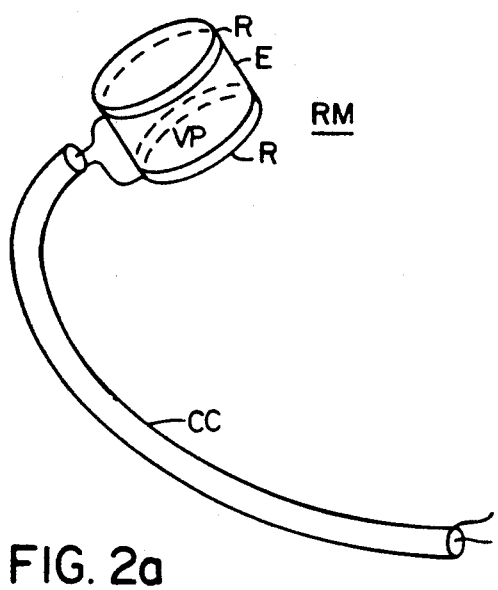
FIGS. 2a and 2b show reference marker devices suitable for use in the method of the present invention.
Figure 2C:
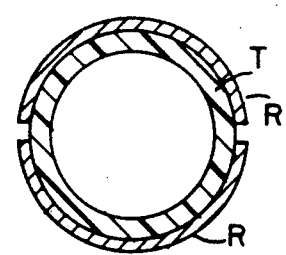
FIG. 2c is a cross-sectional view taken along the lines c—c of FIG. 2b.
Figure 2B:
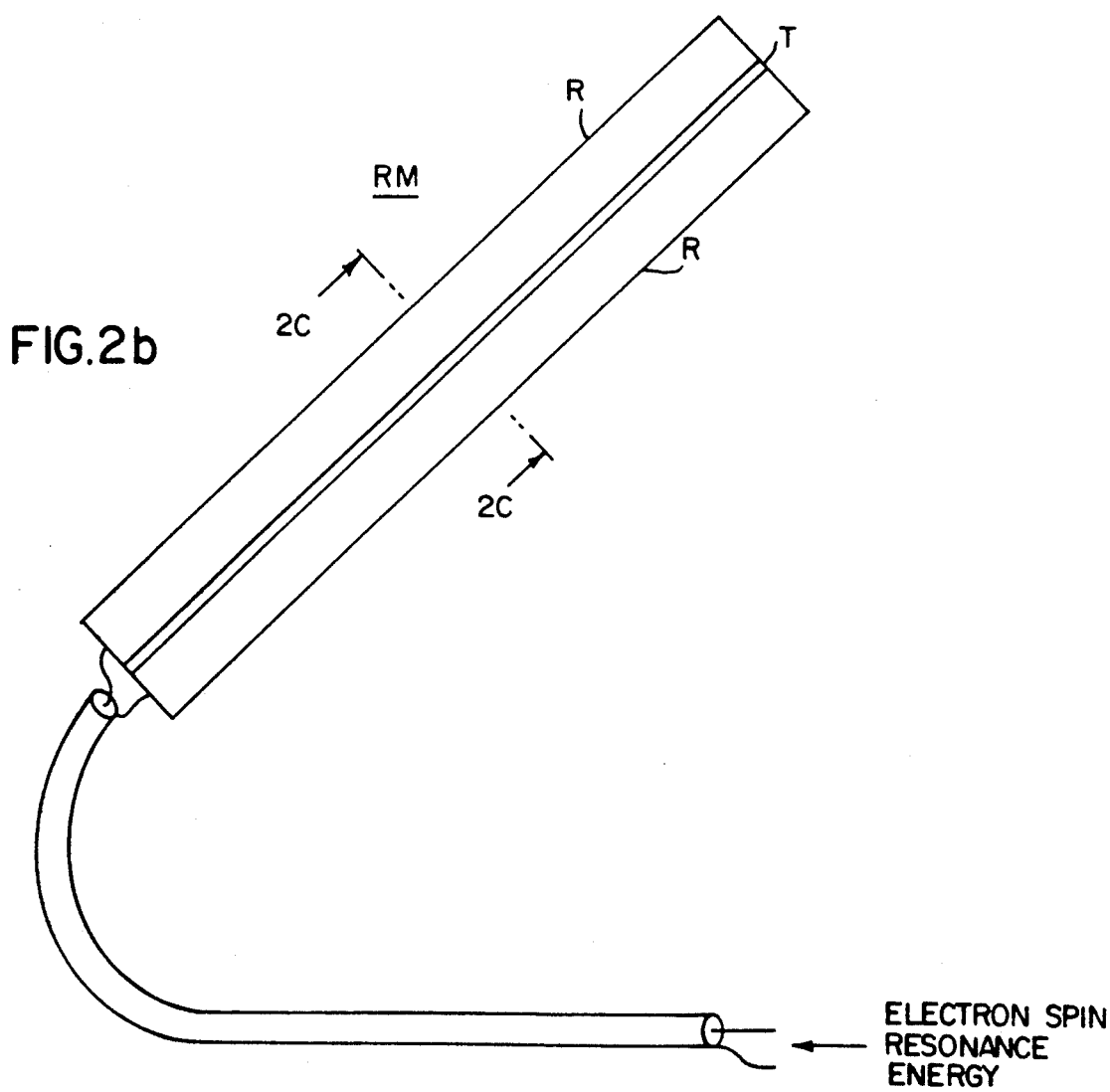

FIGS. 2a, 2b and 2c illustrate in more detail the way of providing the volumes comprising the reference markers RM. FIG. 2a shows a cylindrical volume VP. The volume VP is formed by a tubular container element E formed of plastic or other suitable material. Container element E contains a substance, such as water, containing NMR active nuclei and an ESR relaxant. As an activating agent or relaxant, it is possible to use e.g. nitrogen radicals or paramagnetic ions. In addition to the above-cited references, these have been studied e.g. in the reference Bates RD, Polarization of Solvent Nuclei by Nitroxide Spin Labels at Low Magnetic Fields, J. Magn. Reson., vol. 48, pp. 111-124, 1982. Metal plates R are placed on the ends of tubular element E. The plates R are supplied with electron resource energy by way of a coaxial cable CC which is connected to electron spin resonance energy source ESRE shown in FIG. 1. The reference marker shown in FIG. 2a will generate a dot in the MR image.

FIGS. 1, 2b and 2c show a reference marker capable of generating a line in the MR image. Elongated plastic tube T contains the substance having NMR active nuclei and the ESR relaxant. Arcuate metal plates R are applied to the exterior of plastic tube T. Metal plates R are supplied with electron spin resonance energy by way of coaxial cable CC which is connected to electron spin resonance energy source ESRE in the same manner as described in connection with FIG. 2a.

Because of the NMR signal amplification obtained through the use of DNP, the reference markers shown in FIGS. 2a and 2b, can be small in size.

Figure 3:
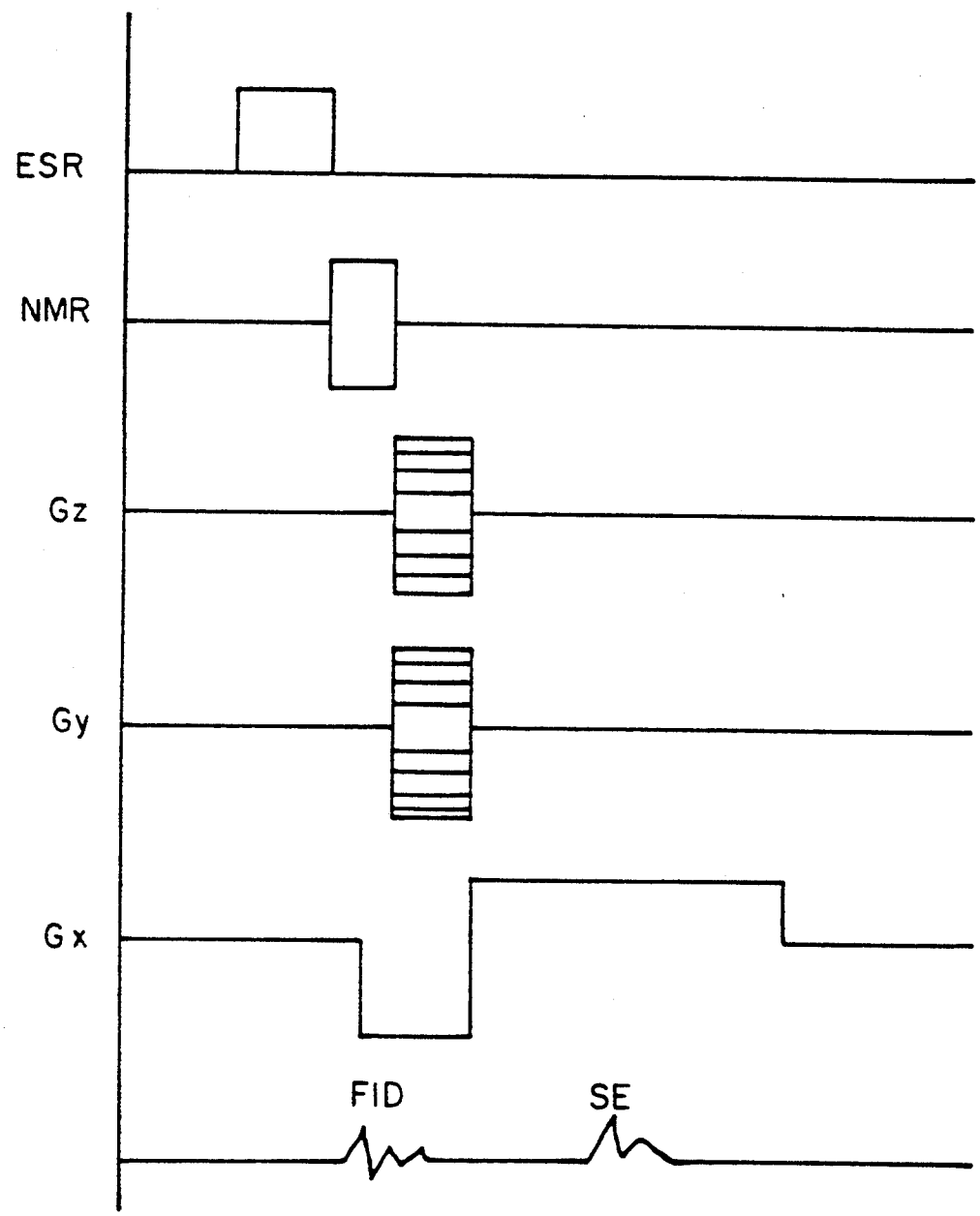
FIG. 3 shows an MRI pulse sequence suitable for use in the present invention.

FIG. 3 shows an imaging method based on a 3-dimensional Fourier imaging technique for recording a position or a location by means of magnetic imaging. The first step comprises providing one or more reference markers RM at a desired location with respect to the object P to be imaged. While reference markers RM may be applied to the exterior of the object, more typically, the object will be inserted into the object to a desired location by means of a tubular operational instrument such as an endoscope-like instrument having an operating channel, or a biopsy-type instrument. The coaxial cable CC extends through the bore or channel of the instrument. One such instrument of this type is shown in co-pending U.S. patent application Ser. No. 428,238, filed Oct. 27, 1989, now abandoned and corresponding issued Finnish Patent 80585.

Before or after the reference marker or markers RM are positioned at the desired location in the object, the object P may be placed in frame F and held by supports S. Thereafter, electromagnet M is energized by magnet current source MC to apply polarizing magnetic field $B_o$ to object P.

The electron spin system of reference marker RM is saturated by means of the ESR frequency electromagnetic energy conducted through the bore or channel of the operational instrument in cable CC. See line ESR of FIG. 3. The nuclear spin system of a reference area is excited with NMR frequency electromagnetic radiation. See line NMR of FIG. 3. Thereafter, the nuclear spin system phase coding is carried out with z- and y-directed gradient pulses, whose timing is marked on lines $G_z$ and $G_y$ of FIG. 3. The NMR signal SE is collected while the x-directed gradient is switched on and the switching timing of this gradient is marked on axis $G_x$. The NMR signal is amplified by DNP resulting from the saturation of the electron spin system. The sequence is repeated as many times as required by phase coding operations and necessary averagings and the final MR image is reconstructed from the resulting signal data.

The advantages gained by the invention in localizing with reference markers RM will be apparent when comparing conventional MRI signals obtained e.g. from a sample of water with a signal obtained by means of MRI activated by means of conventional MRI plus DNP. The amplified signal can be several hundred times more powerful than a signal obtainable without amplification. In other words, if the amplification is by 200 times, a sample of 1 m$^3$ emits a signal that is equally powerful as the signal of a sample of 200 m$^3$. The reduction obtained in imaging time is even more dramatic: an amplified sample can be localized at the same signal-to-noise ratio 40 000 times quicker than a non-amplified sample.

Technology applicable to the generation and transmission of ESR frequency electromagnetic energy has also been described e.g. in the reference: Field et al: Physics and technology of hyperthermia, Martinus Nijhof Publishers, Dordrecht, The Netherlands, 1987.

The invention is not limited to the above embodiments but also other embodiments are conceivable. Naturally, the target nucleus can be any nucleus suitable for NMR tests, such as the nuclei of the NMR active isotopes of hydrogen, phosphor, carbon fluorine and nitrogen. In addition to medical applications, the invention can be applied to the examination of animals, foods and solid pieces.

I claim:

1. A method for providing accurate localization information in an MRX image of an object comprising the steps of:
   providing, at a desired location with respect to the object, a confined volume containing a substance with NMR active nuclei and an ESR relaxant, said relaxant having an electron spin system capable of amplifying the NMR signal emitted by the substance by means of dynamic nuclear polarization, said confined volume being isolated from said object and forming a reference marker;
   applying a polarizing magnetic field to the object and marker;
   supplying electromagnetic energy at an electron spin resonance frequency, which is localized to the confined volume of the marker and which energy is not supplied to portions of the object non-adjacent to the marker, the electromagnetic energy saturating the magnetization of the electron spin system of the relaxant in the marker;
   carrying out an NMR excitation procedure on the object and marker;
   obtaining NMR signal data from the object and marker in which data the NMR signal from the reference marker is amplified by dynamic nuclear polarization; and
   generating an MR image of the object and the reference marker from the obtained NMR data.

2. The method according to claim 1, wherein the steps of providing the confined volume at a desired location with respect to the object is further defined as inserting a container containing the substance and relaxant in the object to form the reference marker.

3. The method according to claim 1 wherein the step of carrying out the NMR excitation procedure is further defined as including the steps of applying NMR frequency electromagnetic radiation to the object and marker and applying gradient magnetic fields to the object and marker.

4. The method according to claim 3 further including the steps of applying gradient magnetic fields in first and second orthogonal directions and obtaining the NMR signal data while applying a gradient magnetic field in a third orthogonal direction.

5. The method according to claim 1 wherein the MRX image is defined in terms of voxels and wherein the step of providing a confined volume is further defined as providing a volume less than a voxel.

6. The method according to claim 1 wherein the step of providing a confined volume is further defined as providing a small, compact volume capable of forming a point in the MR image.

7. The method according to claim 1 wherein the step of providing a confined volume is further defined as providing an elongated volume capable of forming a line in the MR image.

8. A method for providing at least one reference marker in an MRX image of a portion of a human body undergoing examination, said reference marker permitting the obtaining of location information regarding the body portion from the image, said method comprising the steps of:

providing, at a desired location with respect to the body portion, a confined volume containing a substance with NMR active nuclei and an ESR relaxant, said relaxant having an electron spin system capable of amplifying the NMR signal emitted by the substance by means of dynamic nuclear polarization, said confined volume being isolated from said body portion and forming a reference marker;

applying a polarizing magnetic field to the body portion and marker;

supplying electromagnetic energy at an electron spin resonance frequency, which is localized to the confined volume of the marker and which energy is not supplied to portions of the object non-adjacent to the marker, the electromagnetic energy saturating the magnetization of the electron spin system of the relaxant in the marker;

carrying out an NMR excitation procedure on the body portion and marker;

obtaining NMR signal data from the body portion and marker in which data the NMR signal data from the reference marker is amplified by dynamic nuclear polarization; and generating an MR image of the body portion and the reference marker from the obtained NMR data.

9. The method according to claim 8 wherein the step of providing the confined volume at a desired location with respect to the body portion is further defined as inserting a container containing the substance and relaxant in the body potion to form the reference marker.

10. The method according to claim 8 wherein the step of carrying out the NMR excitation procedure is further defined as including the steps of applying NMR frequency electromagnetic radiation to the body portion and marker and applying gradient magnetic fields to the body portion and marker.

11. The method according to claim 10 further including the steps of applying gradient magnetic fields in first and second orthogonal directions and obtaining the NMR signal data while applying a gradient magnetic field in a third orthogonal direction.

12. The method according to claim 8 wherein the MR image is defined in terms of voxels and wherein the step of providing a confined volume is further defined as providing a volume less than a voxel.

13. The method according to claim 8 wherein the step of providing a confined volume is further defined as providing a small, compact volume capable of forming a point in the MR image.

14. The method according to claim 8 wherein the step of providing a confined volume is further defined as providing an elongated volume capable of forming a line in the MR image.

15. The method according to claim 8 further including the step of immobilizing the body portion with a frame applied to the body during the carrying out of the NMR procedure and obtaining the NMR signal data.

* * * * *